United States Patent [19]

Polanyi

[11] Patent Number: 4,516,580

[45] Date of Patent: May 14, 1985

[54] CONTINUOUS BLOOD GAS MONITORING

[76] Inventor: Michael L. Polanyi, Vaughn Hill Rd., Bolton, Mass. 01740

[21] Appl. No.: 335,391

[22] Filed: Dec. 29, 1981

[51] Int. Cl.³ ............................................. A61B 5/00
[52] U.S. Cl. .................................... 123/632; 55/158; 73/19; 73/863.23; 210/321.1; 436/68; 604/43
[58] Field of Search ................. 128/632; 604/43, 93, 604/103; 210/321.1, 321.2, 321.3, 321.4; 73/19, 863.23; 55/158, 159; 422/83, 101; 436/68

[56] References Cited

U.S. PATENT DOCUMENTS

| | | | |
|---|---|---|---|
| 3,438,241 | 4/1969 | McKinley, Jr. | 73/19 X |
| 3,830,106 | 8/1974 | Gardiner et al. | 73/863.23 |
| 4,235,231 | 11/1980 | Schindler et al. | 604/43 |

OTHER PUBLICATIONS

Massaro et al., "Non-Polorographic Blood Gas . . . ", Biomat, Med. Dev., Art. Org., 4 (3 and 4), 385–396, 1976.
Brantigan et al., "A Clinical Catheter . . . " J. App. Phys., vol. 40, No. 3, Mar. 1976, pp. 443–444.
Huchon et al., "Continuous Intravascular Monitoring . . . ", E. J. Intensive Care Med., vol. 2, 23–28, 1976.
Niinikoski et al., "Skeletal Muscle $PO_2$ . . . " Adv. Exp. Med. Biol., vol. 94, pp. 582–586, 1977.
Clark et al., "A Self-Calibrating, . . . Monitor", Adv. Exp. Med. Biol., vol. 94, pp. 31–36, 1977.

Primary Examiner—Lee S. Cohen
Attorney, Agent, or Firm—Michael J. Striker

[57] ABSTRACT

A method and apparatus for measuring of concentrations of components of a fluid mixture. One side of a membrane permeable to the component to be determined is contacted with a sample of the fluid mixture to be analyzed. The second side of the membrane is contacted with a test fluid passing the membrane at different speeds. The resultant properties of the test fluid are determined for the different speeds of flow past the membrane and the measured values allow to determine the concentration or partial pressure of the component in the fluid mixture. The fluid mixture is preferably blood and the components can be oxygen and carbon dioxide. Preferably the membrane provides a spiral path for the test fluid in order to allow employing a more rapid flow of the test fluid past the membrane. Furthermore, such a configuration can be combined with a catheter for hemodynamic blood pressure measurement thereby providing a single probe for continuous monitoring of blood in clinical practice.

12 Claims, 8 Drawing Figures

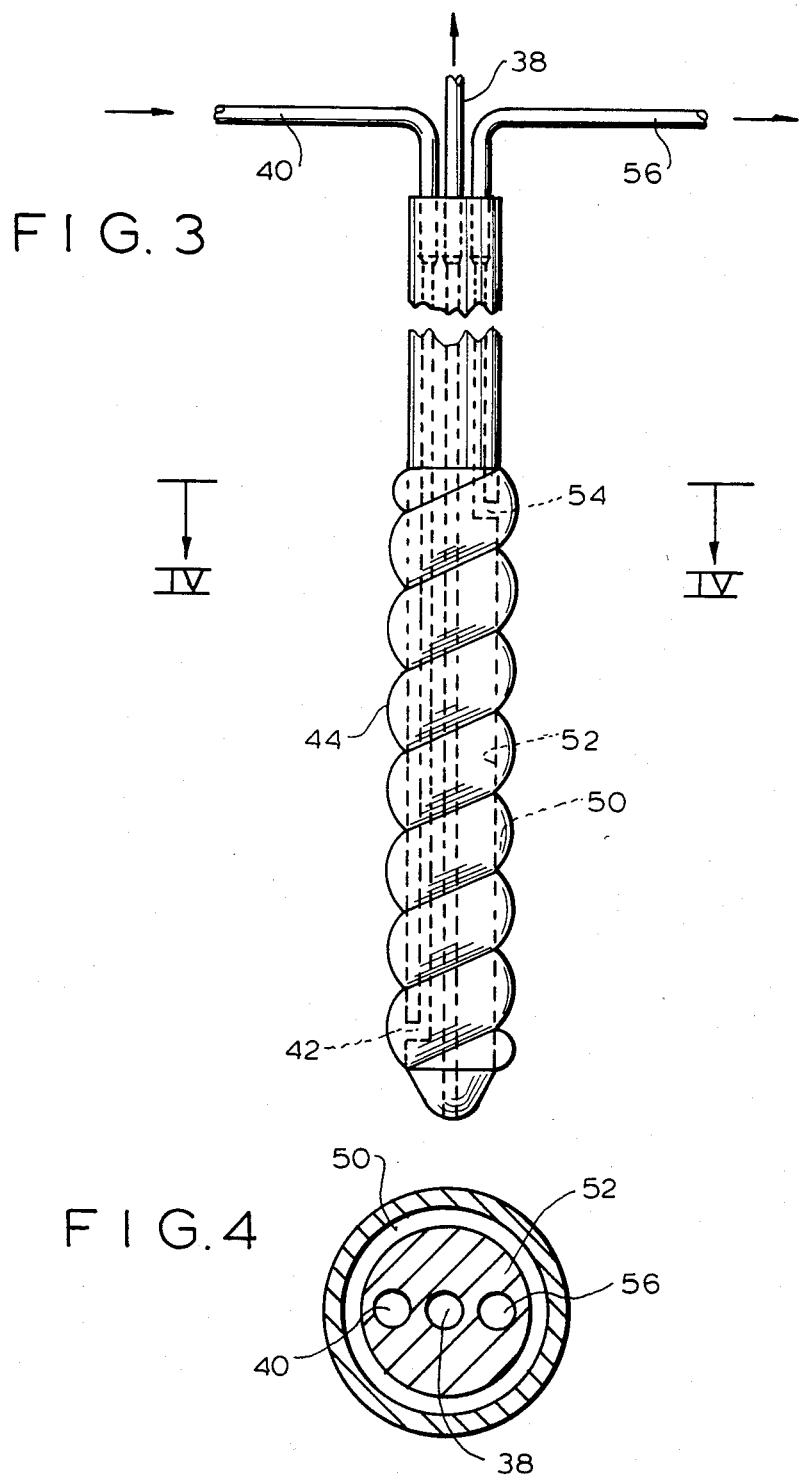

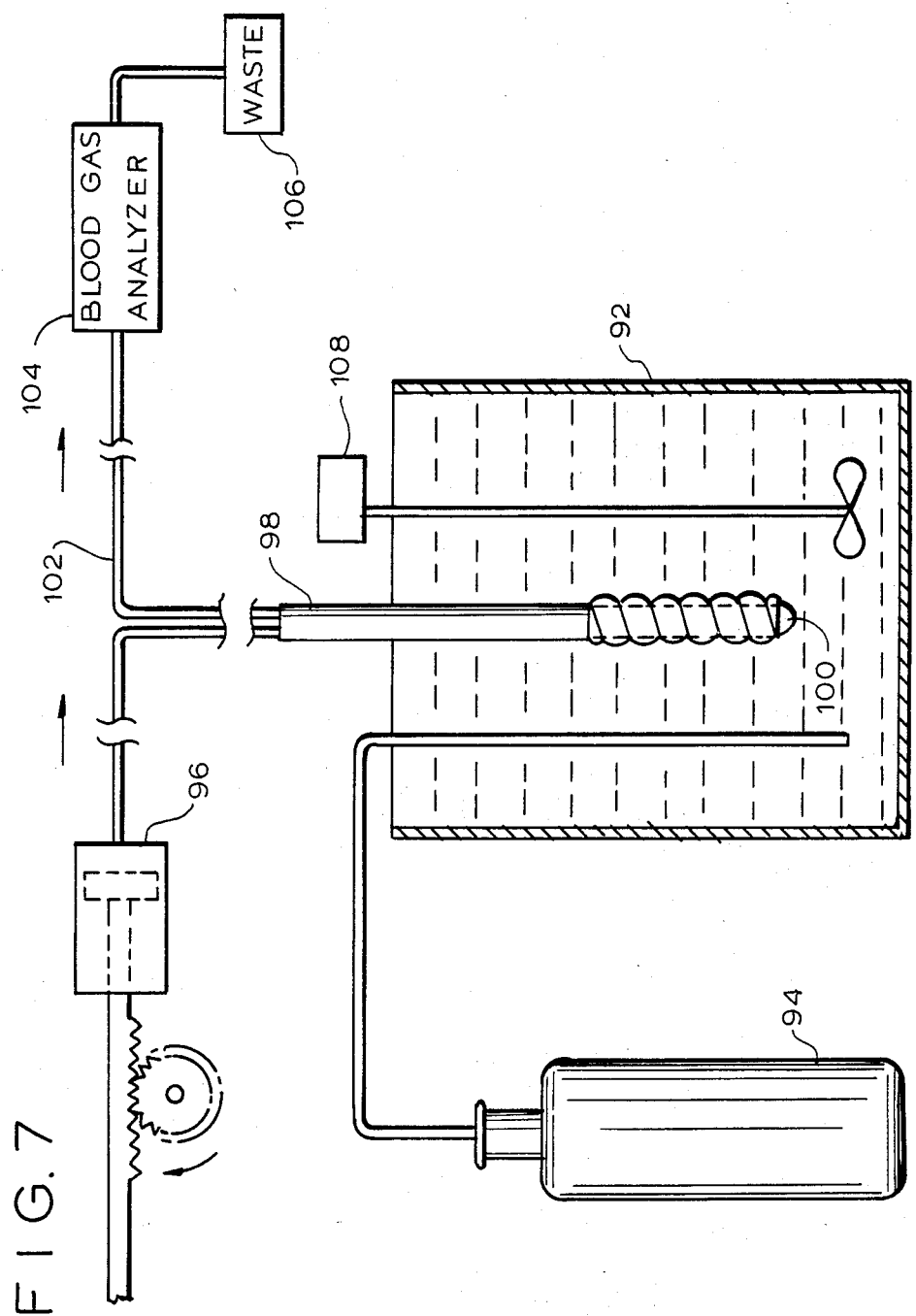

CONTINUOUS BLOOD GAS MONITORING

BACKGROUND OF THE INVENTION

1. Field of the Invention

The present invention relates to a method and apparatus for analytical determination of components in fluid mixtures by employing diffusion of the component to be determined through a membrane.

2. Brief Description of the Background of the Invention Including Prior Art

Blood contains dissolved oxygen ($O_2$) and dissolved carbon dioxide ($CO_2$). The partial pressures, or tensions, are important diagnostic parameters and are frequently measured in clinical settings. Most conventional methods perform such determination in vitro and blood is taken anaerobically via blood vessel puncture and then measured.

Brantigan et al. in Journal of Applied Physiology, Vol. 40, No. 3, March 1976, page 443 show a clinical catheter for continuous blood gas measurements by mass spectrometry. Massaro et al. in Biomat. Med. Dev. Art. Org., Vol. 4, Pages 385–396 (1976) teaches a system for diffusing dissolved blood gases into the lumen of a close-tipped indwelling catheter to approach equilibrium concentration in a carrier gas. Huchon et al. in Europ. Journal Intensive Care Medicine Vol. 2, 23–28 (1976) employs catheter electrodes for determining in vivo the partial pressures of oxygen and carbon dioxide respectively. However, the electrodes as employed could be influenced by other components contained in the blood. Niinikoski et al. in Adv. Exp. Med. Biol. vol. 94, pages 582–592 (1977) disclose implanting a silastic tube between muscles and allowing oxygen to equilibrate through the permeable silastic tube into a hypoxic saline solution. J. S. Clark et al. in Adv. Exp. Med. Biol. Vol 94, pages 31–36 (1977) teach the employing of an in vivo tube containing liquid and coming to equilibrium with body fluid gases.

Thus there are known several methods for determining gas components in blood employing the reaching of equilibrium condition between a body fluid and an external fluid through a membrane followed by an analytical determination of the concentration of the gas component in the external fluid. Such methods are uncertain as it is difficult to assure that equilibrium conditions have been reached and they are furthermore quite time-consuming.

Thus at best conventional systems measure the rate at which blood gases diffuse through a permeable membrane. In general, the correlation of this rate of diffusion with the partial pressure of the gases in the blood is established by calibration of each individual pick-up prior to insertion into the blood stream. Changes in gas transmission of the membrane for example due to deposition of blood components will give erroneous blood gas partial pressure measurements. Thus an unpredictable change in the diffusion rate of the gas through the membrane in a conventional determination would result in errors in the partial pressure determination of the component. This error is independent of the specific analytical determination method applied to the test fluid such as detector mass spectrometry, simple manometry or minaturized polarographic detector mounted on the tip of a catheter.

SUMMARY OF THE INVENTION

1. Purposes of the Invention

It is an object of the present invention to provide a reliable method and apparatus for continuously determining the component concentration in a fluid mixture by allowing the component to diffuse through a membrane into a test fluid.

It is another object of the present invention to determine the partial pressure of gases in blood by diffusion through a membrane in contact with a test fluid without the requirement of calibration measurements and of waiting for the reaching of equilibrium states.

It is a further object of the present invention to provide a system for analyzing in vivo the partial pressures of gases in body liquid, which system is simple and adapted to continuous monitoring as well as to digital evaluation of the resulting data for providing a reading of the desired partial pressures and which decreases the complexity of clinical gas monitoring.

These and other objects and advantages of the invention will become evident from the description which follows.

2. Brief Description of the Invention

The present invention provides a method for measuring the concentration of components in a fluid mixture. One side of a membrane permeable to the component to be determined is contacted with a sample of the fluid mixture to be analyzed. The second side of the membrane is contacted with a test fluid for the component to be determined, with the test fluid contacting the membrane according to a first setting of a relevant parameter. Successively, the second side of the membrane is contacted with the test fluid for the component to be determined, with the test fluid contacting the membrane according to a second setting of a relevant parameter. The resulting properties of the test fluid having contacted the membrane according to different relevant parameters are analyzed for establishing the concentration of the component to be determined from the resulting analytical values of the test fluid.

Preferably, the fluid mixture contains blood. Preferred fluids are liquids. The component to be determined of the fluid mixture can form a gas at room temperature. The component to be determined can be a member of the group consisting of oxygen, carbon dioxide and mixtures thereof.

The test fluid contacting the membrane according to a first setting of a relevant parameter can pass the membrane at a first speed and the test fluid contacting the membrane according to a second setting of a relevant parameter can pass the membrane at a second speed. The test fluid after having passed the membrane at a first speed can be analyzed for the concentration of the component to be determined and the test fluid after having passed the membrane at a second speed can be analyzed for the component to be determined and the resulting analytical data can be processed automatically. The concentration of the component can be obtained substantially by applying the formula $$\left( \frac{P_1 - P_b}{P_o - P_b} \right) Q_1 = \left( \frac{P_2 - P_b}{P_o - P_b} \right) Q_2$$

where $Q_1$ is the speed of the test fluid passing the membrane at a first speed, $Q_2$ is the speed of the test fluid passing the membrane at a second speed, $P_b$ is the partial pressure of the component to be determined in the fluid mixture, $P_o$ is the partial pressure of the component to be determined in the test fluid coming from the pump, $P_1$ is the partial pressure of the component to be determined in the test fluid after having passed the membrane at a first speed, and $P_2$ is the partial pressure of the component to be determined in the test fluid after having passed the membrane at a second speed.

Preferably, the partial pressure $P_o$ of the component to be determined in the incoming test fluid is substantially equal to zero or alternatively corresponds to equilibrium with ambient air. The test fluid can pass through a substantially helical membrane coil having on its outside the fluid mixture.

The test fluid contacting the membrane according to a first setting of a relevant parameter can be left in contact with the membrane for the duration of a first time interval $T_1$ and the test fluid contacting the membrane according to a second setting of a relevant parameter can be left in contact with the membrane for the duration of a second time interval $T_2$. The test fluid having contacted the membrane for a first time interval $T_1$ can be analyzed for the component to be determined and the test fluid having contacted the membrane for a second time interval $T_2$ can be analyzed for the component to be determined. The resulting analytical data can be processed to obtain the partial pressure $P_b$ of the component in the fluid mixture substantially according to the formula $$\left( \frac{P_1 - P_b}{P_o - P_b} \right) 1/T_1 = \left( \frac{P_2 - P_b}{P_o - P_b} \right) 1/T_2$$

where $P_o$ is the partial pressure in the test fluid incoming from the pump of the component to be determined, $P_1$ is the partial pressure of the component to be determined in the test fluid after having been in contact with the membrane for the duration of a first time interval $T_1$, and $P_2$ is the partial pressure of the component to be determined in the test fluid after having been in contact with the membrane for the duration of a second time interval $T_2$.

There is also provided an apparatus for continuous measurement of the concentration of a component in a fluid mixture diffusing through a membrane and received by a test fluid. A pick-up is immersed in the fluid mixture and connected to and receiving test fluid from the pump for the test fluid and the pick-up comprises a spiral path along a membrane for the test fluid to pass with the other side of the membrane being exposed to the fluid mixture. A detector is connected to the efferent part of the pick-up and determines the concentration of the component to be analyzed which passed from the fluid mixture into the test fluid. An evaluation means is connected to the detector for providing suitable readings.

Preferably, the membrane fits tightly over a recessed groove in a tube, which groove carries the test fluid in the pick-up. The membrane can be wound around the outside of a tube having a port for the afferent carrier fluid and a port for the efferent carrier fluid, where the spiral path is provided by a tensioned string running along a spiral and pressing the membrane against the outside of the tube. Alternatively, a tubular membrane can be wound as a spiral path on the outside of a tube and cemented to the tube in this position with an end of the tubular membrane connected to the pump for the test fluid and with the other end of the tubular membrane connected to a detector for the component to be determined.

A hollow tube can be provided inside of the spiral path for the test fluid in order to allow for a simultaneous measurement of the hydrostatic pressure of the fluid mixture with the same pick-up unit.

In the context of the present disclosure, equilibration or equilibrium between gases in the carrier fluid and in the blood mean that the partial pressure of the gas in the blood ($P_b$) and in the carrier ($P_i$) are equal. Allotted equilibrium time is the time for which the carrier is kept in the exchange area, flowing or stationary, and which is deemed sufficiently long for equilibration: $P_b = P_i$.

For any allotted time the partial pressures of the blood gases in the carrier fluid leaving the gas exchange area are less or equal than the corresponding gas pressures in the blood, i.e. $P_i$ is less or equal to $P_b$. As long as the allotted time ($T_i$ or $Q_i$ in the terminology of the present disclosure) is constant, $P_i$ is constant. This constant $P_i$ corresponds to the steady state. In general, in the present invention system $P_1$ and $P_2$ individually are smaller than $P_b$.

It should be noted that a steady state partial pressure $P_1$ or $P_2$ will be indicated by the external gas partial pressure detector only after sufficient time has been allowed to purge the gas exchange area, the efferent tubing, the measuring volumes of the detector of all carrier fluid containing blood gases at a previous level corresponding to a differently set parameter. The time needed to reach the steady state after a change from flow rate $Q_1$ to flow rate $Q_2$ is indicated by the steadiness of the reading of the gas pressure measuring device.

The present invention avoids the disturbing effects of blood clots and of other deposits from the blood since the permeability of the membrane will remain constant during the relatively short time intervals required by the present invention.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention:

FIG. 3 is a view of a schematic representation showing a dual pick-up having the membrane spiral path provided by a string tensioned along a spiral around a tube;

FIG. 4 is a sectional view of the pick-up of FIG. 3 as seen along section line IV—IV.

FIG. 7 is a schematic diagram showing an apparatus for measuring the concentration according to the present invention.

DESCRIPTION OF INVENTION AND PREFERRED EMBODIMENTS

Figure 1:
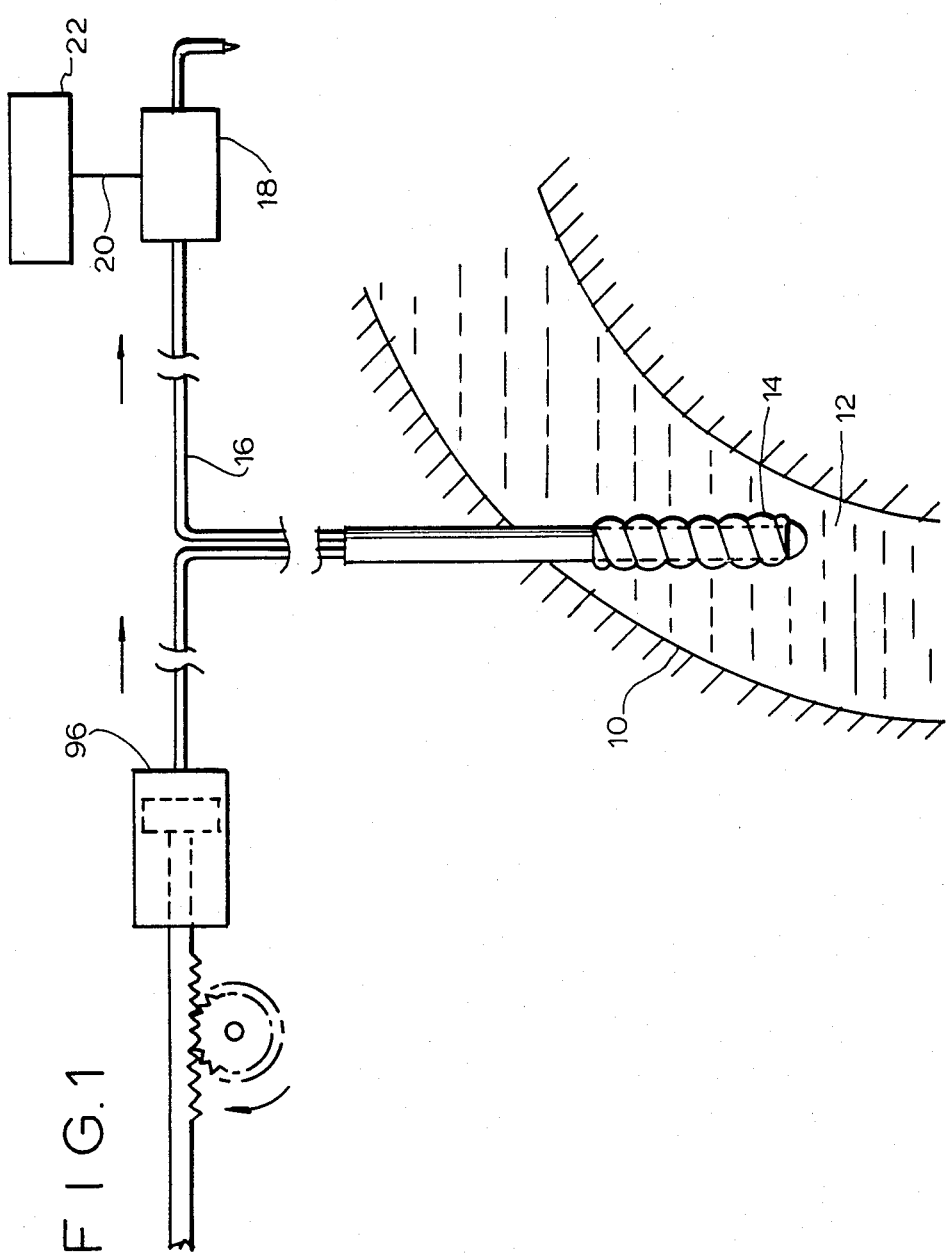
FIG. 1 is a view of a schematic diagram showing components employed in measuring the concentration of a component in a fluid mixture.

In accordance with the present invention the partial pressure of volatile components in blood are determined by diffusing the component through a membrane into a probe and by determining the concentration of the component in the probe for two diffusion situations differing by a suitable parameter.

The diffusion takes place through a gas permeable membrane, which is impermeable to the remainder of the liquid mixture, which mixture preferably contains blood. No equilibrium is assumed to be reached in the diffusion step. The carrier or test fluid in the probe can be stationary or flowing and it can be a liquid or a gas. The test fluid is positively confined to a predetermined path between the outer surface of a catheter and the inner surface of the gas permeable membrane of the pick-up for the component to be determined such as a gas. This path is arranged such as to provide a constant flow pattern of the test fluid over the exchange region near the membrane for the component, which path is virtually independent of the flow rate. In general, the prearranged path will increase the flow of the test fluid or carrier in contact with the permeable membrane as compared to the speed it would have in a conventional system. This improves the efficiency of the gas exchange system. In addition and importantly, the guiding of the path for the test fluid will minimize any configurational changes of the thin gas permeable membrane following changes in blood pressure, test fluid speed and the like.

This maintenance of configuration and flow path are preconditions in the method and apparatus of the present invention for the determination and correlation between partial pressures in a carrier test fluid and in the liquid mixture such as blood.

A central problem in the monitoring of blood gases comprises the obtaining of reliable readings such as for example within plus or minus five percent over protracted monitoring cycles of for example up to 48 hours. The present invention in contrast to conventional methods recalibrates itself after relatively short time intervals such as for example a few minutes and it does not require the attaining of an equilibrium state or the maintenance of an original calibration over the period of monitoring such as for example is required for a mass spectrometer or for a miniaturized electrode.

The test fluid or carrier employed according to the present invention in blood analysis can be a sterile liquid such as normal saline (0.9 percent NaCl in water) solution going through the afferent lumen, passes the gas permeable region and returns from this region via an efferent lumen to an external gas measuring device. While the test fluid as the afferent liquid, or carrier, flows through the component or gas exchange region it picks up gas originating in the blood. The test fluid or carrier enriched with the permeated gases proceeds to the gas detector via an efferent lumen and the partial pressures of the gases in the carrier are measured.

The test fluid or carrier flows through the system preferably at two or more different speeds in a sequence. Typical rates of speed for the test fluid differ by a factor of from about 1.5 to 5 and preferably from about 1.8 to 2.5. Preferred flow rates can be from about 0.01 ml per minute to about 1 ml per minute and more preferred are rates from about 0.05 ml per minute to about 0.3 ml per minute. Each flow rate is maintained for a time sufficiently long to reach steady state. This steady state has been reached when sufficient volume of carrier has been pumped through the system to permit the measurement of gas tensions in the carrier corresponding to a given rate of flow. The sufficiency of such volume depends on the combined volumes of the gas exchange volume, the lumen of the efferent tubing, the volume of the measuring chamber for the exchange as a polarograph and the volume to rinse the whole system of carrier having flown through it previously at a different rate of speed. For example, a rate of 0.1 ml per minute can be maintained for about four minutes and a rate of 0.2 ml per minute can be maintained for about three minutes. Such rates can be reduced by either decreasing the volumes of the several components of the system having a volume or by increasing the flow rates.

The detector can be a conventional detector for the component to be determined. Such detectors can be mass spectrometers, simple manometers and miniaturized polarographic detectors employing Clark electrodes for oxygen $O_2$ and Severinghaus electrodes for carbon dioxide $CO_2$.

After detecting the component in the efferent fluid depending on two values of a parameter of the transport through the membrane into the test fluid, a correlation is performed.

If the carrier circulates at two or more different rates then $Q_1$ is designated as the rate for time duration $t_1$ and $Q_2$ is designated as the rate for a time duration $t_2$. The cycle is repeated continuously. If the afferent carrier contains the component to be measured, the partial pressure of the component in the afferent carrier is designated as $P_o$. The partial pressure or concentration in the fluid mixture such as blood is designated as $P_b$. The evaluation can be performed according to the formula (1)

$$\left( \frac{P_1 - P_b}{P_o - P_b} \right) Q_1 = \left( \frac{P_2 - P_b}{P_o - P_b} \right) Q_2 \qquad (1)$$

The equation (1) can be solved for the only unknown $P_b$. If $P_o$ is not known, a third similar measurement can be made and an analogous correlation involving a measured $P_3$ can give the values of both $P_o$ and $P_b$.

It is preferred that there is negligible gas concentration of the component gas to be determined in the afferent carrier. As the environmental air contains a large percentage of oxygen, there is the possibility that the afferent carrier picks up some oxygen from the air. By equilibrating the afferent carrier with room air, its $O_2$ tension stays constant and is easily determined. If the concentration of the component to be determined in the afferent carrier as expressed by $P_o$ is zero, then equation (1) simplifies to formula (2)

$$\left(1 - \frac{P_1}{P_b}\right) Q_1 = \left(1 - \frac{P_2}{P_b}\right) Q_2 \quad (2)$$

The use of two or more different flow rates permits eliminations of possible errors caused by deposition of blood components on the permeable membrane during prolonged monitoring procedures.

As an alternative, the exchange across the membrane can be performed by the test fluid being stationary across the membrane for different times $T_1$ and $T_2$ in succession. Then the correlation to obtain the gas partial pressure of the component in the fluid mixture can be made according to the formula (3) in the simplified case where $P_o$, the pressure of the component to be determined in the afferent liquid, is zero: $P_o=0$:

$$\left(1 - \frac{P_1}{P_b}\right) 1/T_1 = \left(1 - \frac{P_2}{P_b}\right) 1/T_2 \quad (3)$$

The fluid mixture component or preferably blood gas monitoring system according to the present invention comprises a probe, a circulating test fluid or carrier, a gas tension measuring device and preferably some data processing for obtaining the tensions of the blood gases from tensions determined for components in the test fluid.

The gas measuring device is preferably a bench type detector as compared to miniaturized detectors located in the distal portion of the probe indwelling in the blood stream. The probe according to the present invention is preferably a tube or catheter indwelling in the fluid mixture or preferably blood stream to be analyzed. A portion of the distal end of this tube is covered with a thin membrane of gas permeable and blood impermeable material. Such materials include silastic rubber, polytetrafluoroethylene and celluloid. Silastic is a trademark for compositions comparable in character to milled and compounded rubber prior to vulcanization, but containing organosilicon polymers. Celluloid is a trademark for a plastic consisting essentially of a solid solution of cellulose nitrate and camphor or other plasticizer.

Referring now to FIG. 1, there is shown the wall 10 of a blood vessel confining a blood stream 12. A pick-up probe 14 passes through the blood vessel wall 10 and indwells the blood stream. The pick-up probe 14 is connected via conduits 16 to a gas measuring device and pump 18 and the gas measuring device is connected via line 20 to data evaluation apparatus 22, which preferably comprises a computer and a display.

A pick-up in principle useful according to the invention method is the pick-up disclosed in Clark et al., Adv. Exp. Med. Biol., Vol 94, Pages 31 to 36 (1977), which is included in this disclosure by reference. However, Clark et al. make no provision for confining the fluid carrier along a defined path. As taught by Clark et al. the path of the fluid carrier might change with changing flow rates and/or by erratic bulging of the gas permeable tubing.

Figure 2:
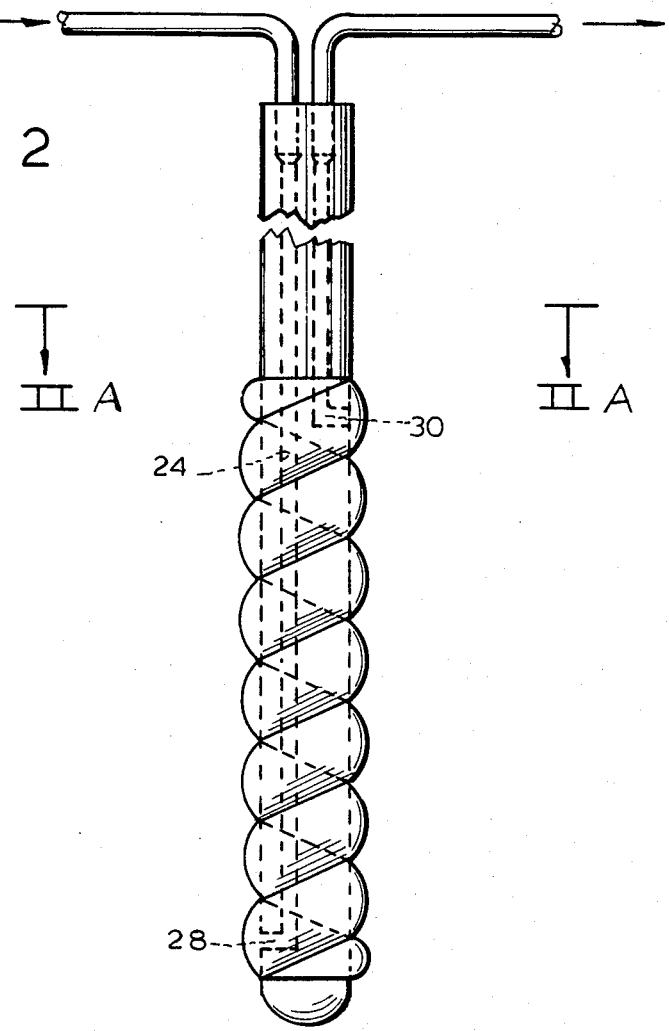
FIGS. 2 and 2a are views of a schematic diagram showing a simple pick-up according to the present invention for determining the partial pressure of gases in fluid mixtures.
Figure 2A:
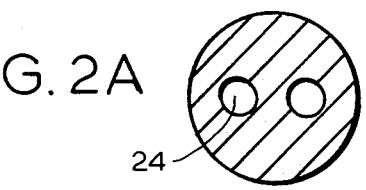

Referring now to FIG. 2, there is shown a portion 24 of the distal end of the tube or catheter indwelling in the blood stream, which is covered by a tightly fitting gas permeable membrane 26. The gas exchange carrier is confined to a prescribed path for the carrier between afferent port 28 and efferent port 30. The flow of the carrier fluid is restricted to a relatively narrow meandering path and preferably a spiral path between the outer surface of the catheter and the inner surface of the membrane, which inner surface in general is not in direct contact with the blood. The preferred meandering path can be obtained by cementing the membrane to the catheter along a narrow seam of appropriate geometry (FIG. 6), by providing an appropriate relief pattern on the catheter surface over which the permeable membrane is secured (FIG. 5) or by spiralling thread wound on the outside of a gas permeable tubing tight fitting on a cylinder body with afferent port and efferent port connected (FIGS. 2 and 3).

The embodiment of FIG. 3 shows a pick-up probe for simultaneous measurement of the partial pressure of components of the blood stream and of the hemodynamic pressure.

The lower end 36 of a tube 52 is inserted into the fluid mixture to be analyzed. The upper end 38 of the tube is connected to a manometer. A pump presses carrier fluid into the afferent input and the carrier fluid reaches the afferent port 42. A tightly fitting membrane 44 is disposed around the tube and a spiral path for the carrier fluid under the membrane is defined by a string 48 tensioned along a spiral line around the membrane. After passing through the spirally defined path between membrane 44 and tube 52 the carrier fluid 50 with the diffused gas component to be analyzed reaches the efferent port 54 and is carried away through the efferent tube 56 to a detector for the component of interest.

FIG. 4 shows a sectional view of the pick-up probe of FIG. 3 along section line IV—IV. The position of the afferent tube 40 and of the efferent tube 56 relative to the supporting tube 52 can be recognized.

Figure 5:
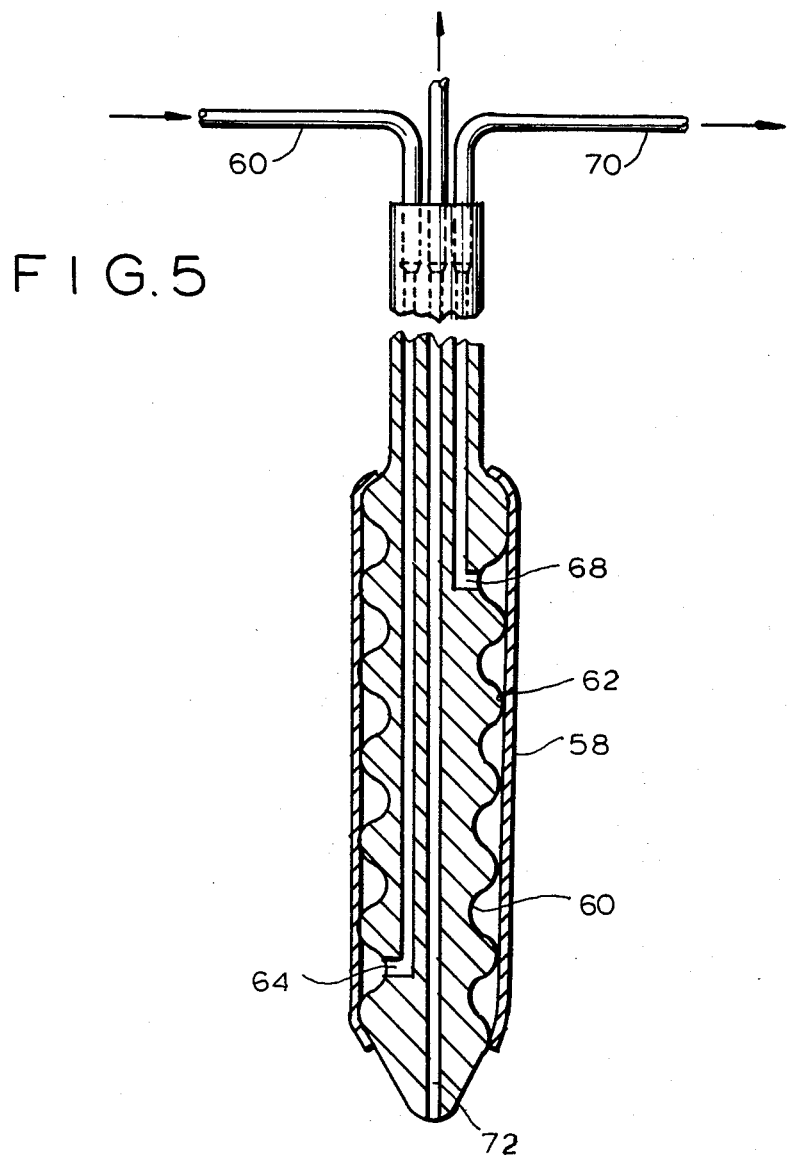
FIG. 5 is a view of a schematic representation showing a dual pick-up with a tightly fitting membrane around a tube with a helical groove for confining the test fluid.

FIG. 5 shows an in part sectional view of an embodiment where a tightly fitting membrane tube 58 covers a spiral groove 60 area in a support tube 62. The spiral groove 60 is connected to an afferent port 64 and an afferent line 66 and also to an efferent port 68 and to an efferent line 70. This embodiment again provides for dual measurement by having an inner tube 72 available for making a hemodynamic blood pressure measurement.

Figure 6:
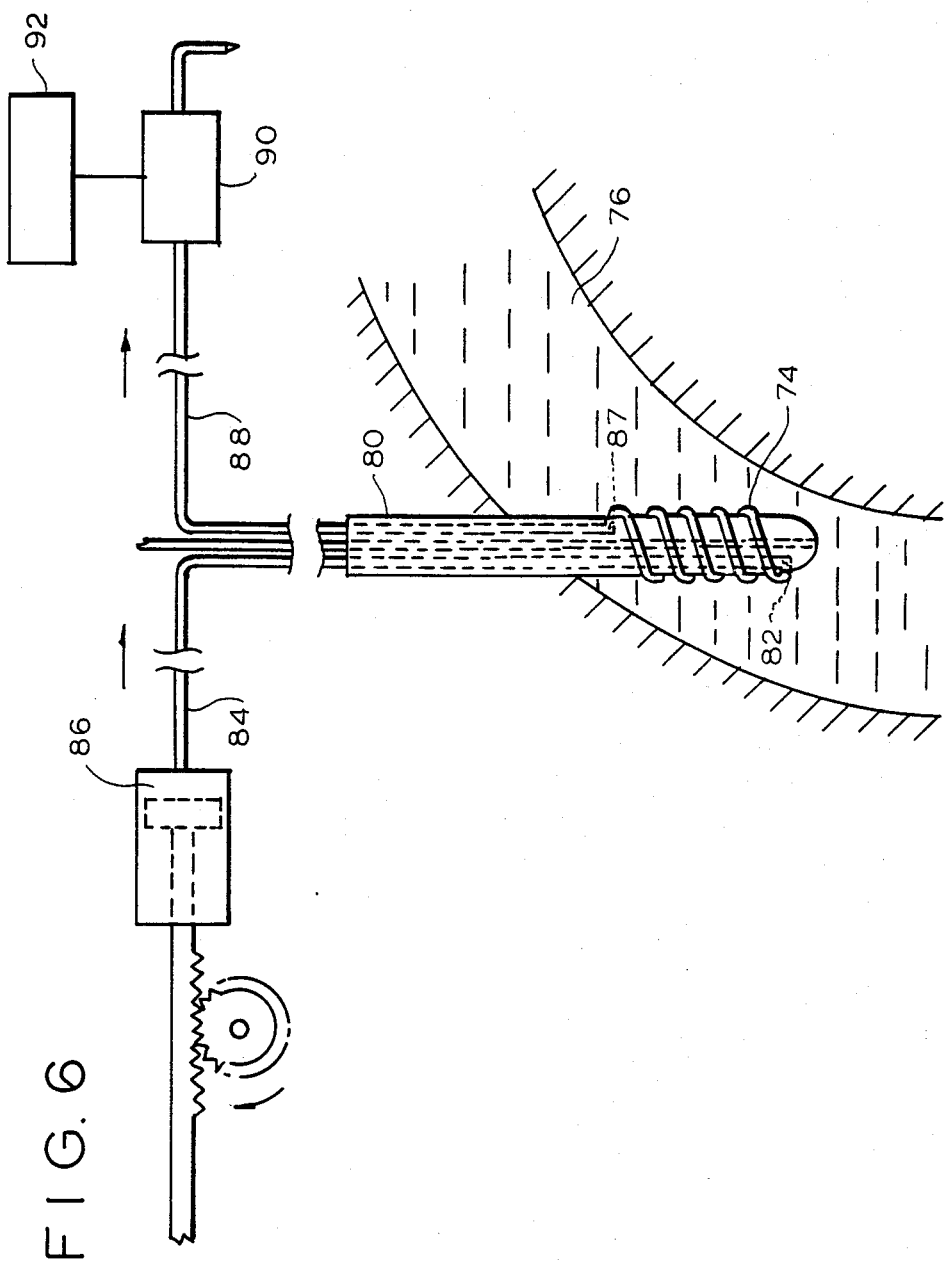
FIG. 6 is a view of a schematic representation showing a dual pick-up with a tubular membrane spirally wound around a tube and cemented to it.

FIG. 6 shows a view of an embodiment with a tubular membrane 74 for exchange of a gas component of the blood 76 flowing through a blood vessel 78. The membrane 74 is cemented to a tube 80 and connected via the afferent port 82 and a conduit 84 to a pump 86 for the test fluid serving as a carrier. The second end of the tubular membrane 74 is connected via an efferent port 86 and an efferent conduit 88 to a partial pressure measuring polarographic device 90. A computer 92 is connected to the polarographic device 90 to receive the data for providing appropriate readings.

In the embodiments shown a relatively long and continuous path of lower resistance is employed along which the carrier fluid will circulate and find or "tunnel" its way from afferent port to efferent port in one direction in a defined pattern. The speed of the permissible carrier flow through the exchange area will be proportional to the length of the path employed.

The pick-up of the present invention preferably is constructed as a dual function pick-up permitting the measuring of blood pressure and of blood gas partial pressure at the same time. Such dual function considerably reduces the complexity of introducing these pickups into the blood stream. FIGS. 3 to 6 refer to embodiments provided with simultaneous measurement capability for hydrostatic blood pressure. In clinical practice blood pressure and blood gas partial pressure are monitored concurrently and a single probe for this dual purpose is highly desirable.

Conventionally the pick-up for hemodynamic blood pressure monitoring invasively consists of a tube or catheter indwelling in the blood vessel, vein, artery or heart. The tube is open at the distal end and is connected at the proximal end to a manometer. The catheter lumen is filled with a sterile liquid column, in general normal saline, which transmits the pressure of the blood from the distal end of the catheter to the manometer.

The dual purpose probes of FIGS. 3 to 6 provide the advantages of a single operation introducing both sensors and no portion is protruding past the open end of the blood pressure pick-up.

It is an important feature of the present invention that the fluid carrier flowing through the pick-up follows a defined path, which is preferably maximized for exchange of the gas component between blood and carrier fluid by insuring that the whole permeable surface is flushed by the flowing carrier. The spiralling path of the membrane provided according to the present invention is longer than a direct path between afferent port and efferent port. Such longer path allows to increase the speed of flow of the carrier fluid through the membrane exchange area.

EXAMPLE I

A pick-up according to FIG. 2 was inserted into the blood. A saline solution was passed through the pick-up as a carrier fluid at the rate $Q_1$ of 0.1 ml per minute for a time $t_1$ of 5 minutes and at the rate $Q_2$ of 0.2 ml per minute for a time $t_2$ of 3 minutes. The partial pressure $P_1$ of carbon dioxide was determined to 38 mmHg and the partial pressure $P_2$ of carbon dioxide was determined to 29 mmHg.

The carbon dioxide pressure $P_b$ of the blood was found to be $$P_b = \frac{P_1^2 - P_oP_2}{2P_1 - (P_2 + P_o)} = \frac{29^2}{2.29 - 38} = 42.05 \text{ mmHg}$$

Compared to the value of 42.05 mmHG found according to the invention method conventional measurement resulted in a value of 43.5 mmHg.

The conventional measurement was carried out in vitro with normal saline equilibrated with a mixture of $CO_2$, $O_2$ and $N_2$.

EXAMPLE II

This example provides an in vitro determination of the gas pressure of carbon dioxide and oxygen. The electrode was calibrated and the apparatus as shown in FIG. 7 was constructed. The water bath in the 600 ml beaker 92 was at a temperature of 20° C. and filled with distilled water, and continuously stirred with stirring mechanism 108 and tonometered with commercial mixtures of oxygen, carbon dioxide and nitrogen in known proportions provided by a gas supply tank 94. The gas mixture contained about 5 percent carbon dioxide, 10 percent oxygen and 85 percent nitrogen. Normal saline, at 20° C. equilibrated with room air, was drawn up in a 50 ml syringe and placed in a Harvard infusion pump 96. The normal saline carrier fluid was pumped through a 122 cm, 1.6 mm inner diameter, PVC (polyvinylchloride) afferent tubing 98 leading to the test probe 100. The test probe corresponded to the construction of FIG. 2. The efferent tubing 102 had a length of 90 cm, an inner diameter of 0.4 mm, was constructed from gas impermeable stainless steel and led the carrier outflow from the probe to the common measuring chamber of the blood gas analyzer, which measured concurrently both the oxygen and carbon dioxide carrier gas tension values. The blood gas analyzer was a commercial unit designated as Corning 161. The waste was removed from the blood analyzer 104 to a waste collection unit 106. The flow rates of the pump were in a 1:2 relationship and the speeds of 100 microliter per minute and 200 microliter per minute, or alternatively 50 microliter per minute and 100 microliter per minute were employed. Each flow rate was maintained until a steady-state reading was observed on the chart recorder at which time the second corresponding flow rate was selected.

As $Q_1/Q_2 = 2$ the relationship $$P_G = \frac{P_1^2 - P_oP_2}{2P_1 - (P_2 + P_o)}$$

holds and the following results were obtained

|  | cc/minute | | pressure mm of Hg | | | | |
| --- | --- | --- | --- | --- | --- | --- | --- |
|  | $Q_1$ | $Q_2$ | $P_0$ | $P_1$ | $P_2$ | $P_b$ | $P_{bx}$ |
| $CO_2$ | 0.10 | 0.05 | 0 | 29 | 38 | 42.5 | 43.5 |
| $O_2$ | 0.20 | 0.10 | 145 | 76 | 57.6 | 50.91 | 51.5 | where $P_b$ is the value determined and calculated in accordance with the present invention and where $P_{bx}$ is the actual value (independently measured) of the gas tensions in the solution equilibrated with $O_2$, $CO_2$ and $N_2$.

It will be understood that each of the elements described above, or two or more together, may also find a useful application in other types of system configurations and fluid component determining procedures and body liquid determinations differing from the types described above.

While the invention has been illustrated and described as embodied in the context of a pick-up probe for determination of partial pressures of gases in blood and of a method for determining component concentrations in fluid mixtures, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for measuring the concentration of components of a fluid mixture comprising contacting one side of a membrane permeable to the component to be determined with a sample of the fluid mixture to be analyzed;

contacting the second side of the membrane with a test fluid for the component to be determined with the test fluid contacting the membrane according to a first setting of a relevant parameter;

contacting successively the second side of the membrane with the test fluid for the component to be determined with the test fluid contacting the membrane according to a second setting of a relevant parameter;

analyzing the resultant properties of the test fluid having contacted the membrane according to the first setting of a relevant parameter;

analyzing the resultant properties of the test fluid having contacted the membrane according to the second setting of a relevant parameter, for establishing the concentration of the component to be determined from the resulting analytical values of the test fluid obtained from both analyzing the resultant properties of the test fluid having contacted the membrane according to both settings of a relevant parameter.

2. The method according to claim 1 wherein the fluid mixture is blood.

3. The method according to claim 1 wherein the fluids are liquids.

4. The method according to claim 1 wherein the component to be determined of the fluid mixture forms a gas at room temperature.

5. The method according to claim 1 wherein the component to be determined is a member of the group consisting of oxygen, carbon dioxide and mixtures thereof.

6. The method according to claim 1 wherein the test fluid contacting the membrane according to a first setting of a relevant parameter is passing the membrane at a first speed and wherein the test fluid contacting the membrane according to a second setting of a relevant parameter is passing the membrane at a second speed.

7. The method according to claim 6 further comprising analyzing the test fluid after having passed the membrane at a first speed for the concentration of the component to be determined;

analyzing the test fluid after having passed the membrane at a second speed for the concentration of the component to be determined; and processing the resulting analytical data automatically.

8. The method according to claim 6 wherein the concentration of the component is obtained substantially by applying the formula $$\left(\frac{P_1 - P_b}{P_o - P_b}\right) Q_1 = \left(\frac{P_2 - P_b}{P_o - P_b}\right) Q_2$$

where $Q_1$ is the speed of the test fluid passing the membrane at a first speed;

$Q_2$ is the speed of the test fluid passing the membrane at a second speed;

$P_b$ is the partial pressure of the component to be determined in the fluid mixture;

$P_o$ is the partial pressure of the component to be determined in the incoming test fluid;

$P_1$ is the partial pressure of the component to be determined in the test fluid after having passed the membrane at a first speed; and $P_2$ is the partial pressure of the component to be determined in the test fluid after having passed the membrane at a second speed.

9. The method according to claim 6 wherein the partial pressure $P_o$ of the component to be determined in the incoming test fluid is substantially equal to zero.

10. The method according to claim 6 further comprising passing the test fluid through a substantially helical membrane coil having on its outside the fluid mixture.

11. The method according to claim 1 wherein the test fluid contacting the membrane according to a first setting of a relevant parameter is left in contact with the membrane for the duration of a first time interval $T_1$; and where the test fluid contacting the membrane according to a second setting of a relevant parameter is left in contact with the membrane for the duration of a second time interval $T_2$.

12. The method according to claim 11 further comprising analyzing the test fluid having contacted the membrane for a first time interval $T_1$ for the component to be determined; analyzing the test fluid having contacted the membrane for a second time interval $T_2$ for the component to be determined; and processing the resulting analytical data to obtain the partial pressure $P_b$ of the component in the fluid mixture substantially according to the formula $$\left(\frac{P_1 - P_b}{P_o - P_b}\right) 1/T_1 = \left(\frac{P_2 - P_b}{P_o - P_b}\right) 1/T_2$$

where $P_o$ is the partial pressure in the incoming test fluid of the component to be determined;

$P_1$ is the partial pressure of the component to be determined in the test fluid after having been in contact with the membrane for the duration of a first time interval $T_1$; and $P_2$ is the partial pressure of the component to be determined in the test fluid after having been in contact with the membrane for the duration of a second time interval $T_2$.

* * * * *

UNITED STATES PATENT AND TRADEMARK OFFICE
CERTIFICATE OF CORRECTION

PATENT NO. : 4,516,580  
DATED : May 14, 1985  
INVENTOR(S) : Michael L. Polanyi Page 1 of 2

It is certified that error appears in the above—identified patent and that said Letters Patent is hereby corrected as shown below:

Column 2, line 65  
Column 6, line 55 and Claim 8    Formula should read as follows:

$$\left(\frac{P_1 - P_b}{P_o - P_b}\right)^{Q1} = \left(\frac{P_2 - P_b}{P_o - P_b}\right)^{Q2}$$

Column 3, line 38  
Claim 12

$$\left(\frac{P_1 - P_b}{P_o - P_b}\right)^{1/T_1} = \left(\frac{P_2 - P_b}{P_o - P_b}\right)^{1/T_2}$$

Column 7, line 7

$$\left(1 - \frac{P_1}{P_b}\right)^{Q1} = \left(1 - \frac{P_2}{P_b}\right)^{Q2}$$

UNITED STATES PATENT AND TRADEMARK OFFICE
CERTIFICATE OF CORRECTION

PATENT NO. : 4,516,580
DATED : May 14, 1985
INVENTOR(S) : Michael L. Polanyi

It is certified that error appears in the above-identified patent and that said Letters Patent is hereby corrected as shown below:

Column 7, line 25 Formula should read as follows:

$$\left(1 - \frac{P_1}{P_b}\right)^{1/T_1} = \left(1 - \frac{P_2}{P_b}\right)^{1/T_2}$$

Signed and Sealed this

Twentieth Day of May 1986

[SEAL]

Attest:

DONALD J. QUIGG

Attesting Officer

Commissioner of Patents and Trademarks